(12) United States Patent
Jung, Jr. et al.

(10) Patent No.: US 6,290,693 B1
(45) Date of Patent: Sep. 18, 2001

(54) SWIVEL TIP ASSEMBLY AND CATHETER USING SAME

(75) Inventors: Eugene J. Jung, Jr.; James Savage, both of San Diego; Erich H. Wolf, Vista, all of CA (US)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/354,992

(22) Filed: Jul. 16, 1999

Related U.S. Application Data

(60) Continuation-in-part of application No. 09/436,666, filed on Nov. 10, 1999, which is a division of application No. 09/118,308, filed on Jul. 16, 1998, now abandoned.

(51) Int. Cl.$^7$ .................................................. A61M 25/16
(52) U.S. Cl. ...................... 604/535; 600/585; 604/103.04
(58) Field of Search ...................... 604/103.04, 533–537; 600/434, 585

(56) References Cited

U.S. PATENT DOCUMENTS 5,546,958 * 8/1996 Thorud et al. ..................... 600/585

* cited by examiner

Primary Examiner—Anhtuan T. Nguyen
(74) Attorney, Agent, or Firm—Leydig, Voit & Mayer, Ltd.

(57) ABSTRACT

A swivel tip assembly (100) includes a housing (110) having a passageway (128) with proximal (112) and distal (114) openings. Spherical member (106) and bushing (108), which is captured by the housing (110), provide a swivel joint. A wire (102), which is coupled to the spherical member (106), is attached to the distal end of a catheter (50). The swivel joint allows the housing (110) to swivel or rotate freely thereby minimizing the opportunity of grabbing the guide wire (116) as the catheter (504) is being pushed or pulled along the guide wire (116).

16 Claims, 7 Drawing Sheets

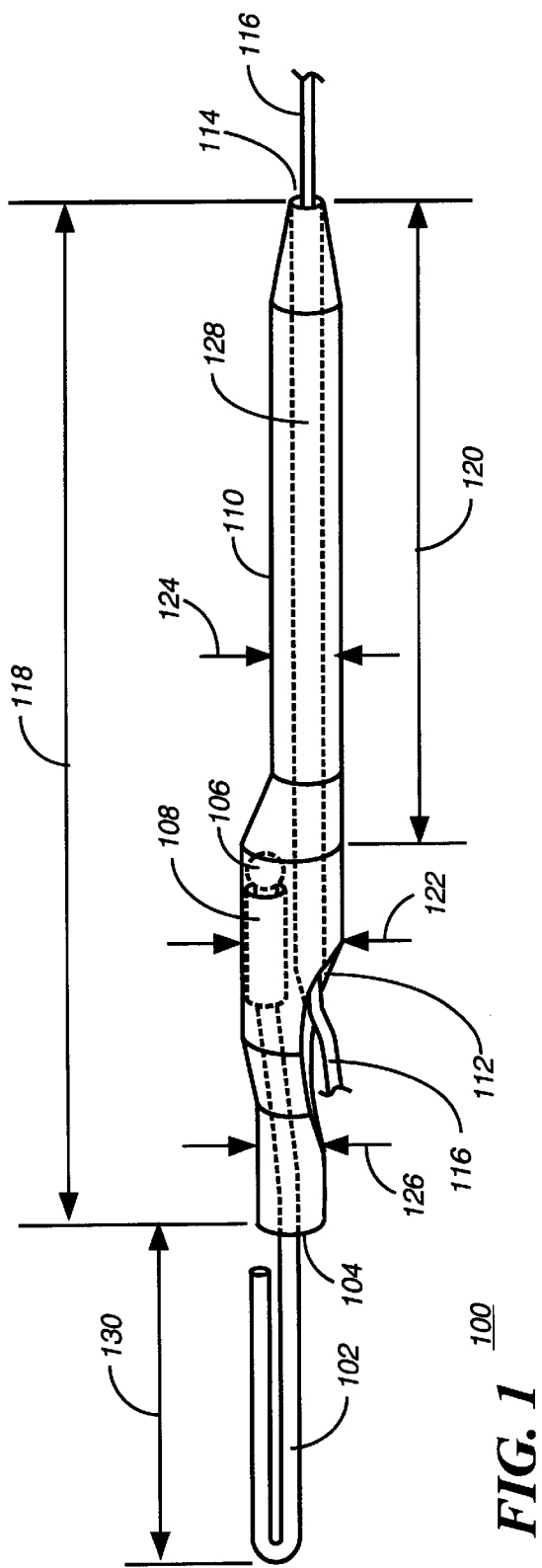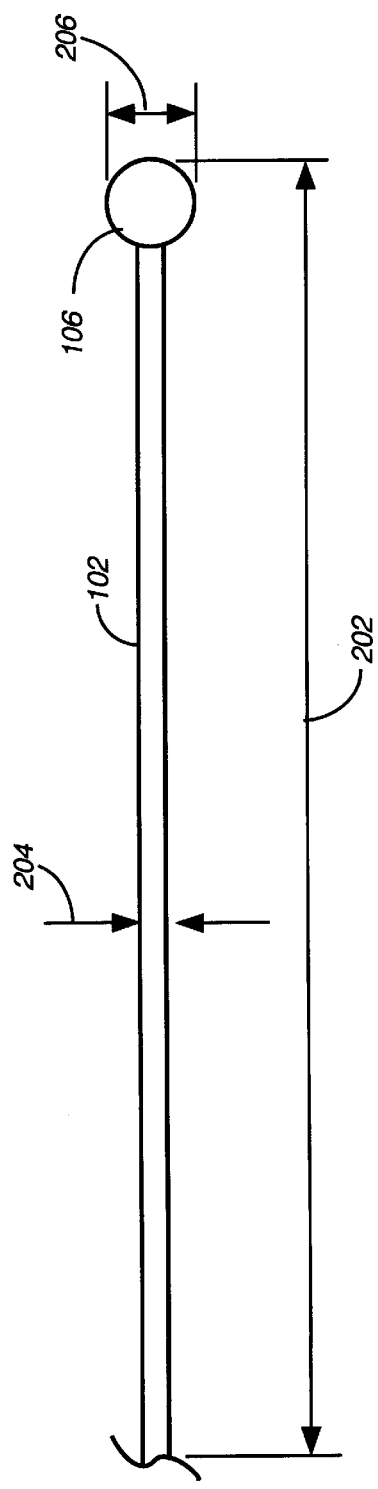

US 6,290,693 B1

SWIVEL TIP ASSEMBLY AND CATHETER USING SAME

This application is a Continuation-in-Part of the currently pending U.S. Application Ser. No. 09/436,666 filed Nov. 11, 1999 which is a division of Application Ser. No. 09/118,308, filed on Jul. 16, 1998, abandoned.

FIELD OF THE INVENTION

This invention relates in general to the field of medical devices, more particularly, this invention relates to a swivel tip assembly and catheter using the swivel tip assembly.

BACKGROUND OF THE INVENTION

Catheters are well known in the medical field. The typical procedure for inserting a catheter into a patient is to first feed a guide wire into the patient until the distal end of the guide wire has reached a target location inside the patient, for example, a portion of a blood vessel that has a stenosis. Once the guide wire is in place, a catheter is feed through the proximal end of the guide wire. The catheter is then feed into the patient and tracked along the guide wire until the catheter has also reached the target location.

In a exemplary application, a percutaneous transluminal coronary angioplasty (PTCA) catheter is feed through a guide wire that has been inserted into a patient until the balloon carried by the PTCA catheter has reached the target location (e.g., location of stenosis). The balloon is then inflated in order to expand the vessel at the location of the stenosis. After the balloon has been inflated at the target location, it is deflated and the catheter is pulled back from the target area.

There are in general two main ways by which catheters track over a guide wire, the first is an "over-the-wire" design in which the guide wire lumen extends from the far distal tip of the catheter to the far proximal end. The second is a monorail system where the guide wire lumen is shorter than the catheter.

The advantage of the monorail (also call "rapid exchange") design is that the shorter guide wire lumen allows a single operator to change catheters conveniently. In one embodiment of the monorail system, the guide wire lumen is very short in length, for example, less than 2 centimeter (cm) and the guide wire lumen is positioned at the far distal tip of the catheter. In these catheters where you have a short distal exchange guide wire lumen, by construction the guide wire exit portion (the proximal end guide wire port) may be in the tortuous portion of the vessel causing the catheter to potentially snag the guide wire. The problem that some times occurs when such a catheter is being pushed or pulled back along the guide wire is that the catheter may grab the guide wire and drag it along, especially when the catheter is being moved along a tight bend in the vessel. This grabbing or snagging of the guide wire by the catheter affects the proper placement of the guide wire. The correction of this problem is for the physician to work the guide wire back to its proper location. This sometimes may take a long period of time to accomplish, especially if the guide wire has gone through several tight bends. Given that time is of the essence when a patient is undergoing a surgical procedure such as PCTA, a need exists in the art for a catheter, which can minimize the above-mentioned problem.

BRIEF DESCRIPTION OF THE DRAWINGS

FIG. 1 shows a swivel tip housing attached to a swivel wire in accordance with the preferred embodiment of the invention.

FIG. 2 shows the swivel wire and ball tip shown in FIG. 1.

DETAILED DESCRIPTION OF THE PREFERRED EMBODIMENT

Figure 3:
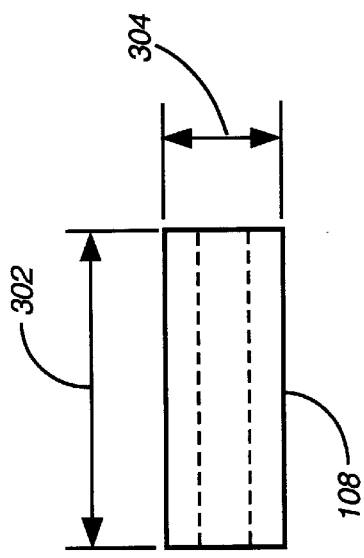
FIG. 3 shows the swivel bushing shown in FIG. 1.

Referring now to the drawings and in particular to FIG. 1 there is shown a swivel tip assembly 100 in accordance with the preferred embodiment. The swivel tip assembly 100 includes a housing 110 formed from high-density polyethylene ("HDPE"). Although HDPE is used in the preferred embodiment, the swivel tip housing 110 could be formed of other well-known materials used for medical applications as known in the art. The swivel tip housing 110 includes a guide wire passageway or lumen 128. The guide wire passageway 128 has proximal 112 and distal 114 apertures or openings. The guide wire passageway 128 is used for receiving a guide wire 116. Once the guide wire 116 is inserted into passageway 128 a catheter (shown in FIG. 5 as one example) having the swivel tip assembly 100 is tracked along the guide wire 116 until it reaches the target location.

The use of the swivel tip assembly 100 helps reduce the snagging or grabbing of the guide wire 116 by the catheter as previously mentioned since the swivel tip housing 110 is able to rotate about wire 102 and helps maintain a loose coupling to the guide wire 116. This is especially helpful in reducing snagging of the guide wire while the catheter is being maneuvered through one or more tight turns along a vessel. The ability of the swivel tip housing 110 to freely swivel or rotate about wire 102 helps reduce any binding forces formed between the catheter and the guide wire as the catheter tracks along the guide wire.

In the preferred embodiment, swivel tip housing 110 has an overall length 118 of approximately 15 millimeters (0.59-inch). Guide wire passageway or lumen 128 has a diameter of approximately 0.432 mm (0.017-inch) and the distal portion of housing has an outside diameter 124, at the noted location, of approximately 0.61 mm (0.024inch). The outside diameter of housing 110 at its proximal end 126 is also approximately 0.61 mm (0.024 inch). There is a slight bulge in swivel tip housing 110 at 122 where the outside diameter is approximately 0.86mm (0.034 inch). The distal end of the housing 120 is approximately 10 mm (0.39 inch) in length. The proximal guide wire opening 112 of the housing is angled (also referred to as a "skive") to further reduce the possibility of the guide wire 116 hanging up with the swivel housing 110 as the swivel tip housing is navigated through tight turns.

Figure 12:
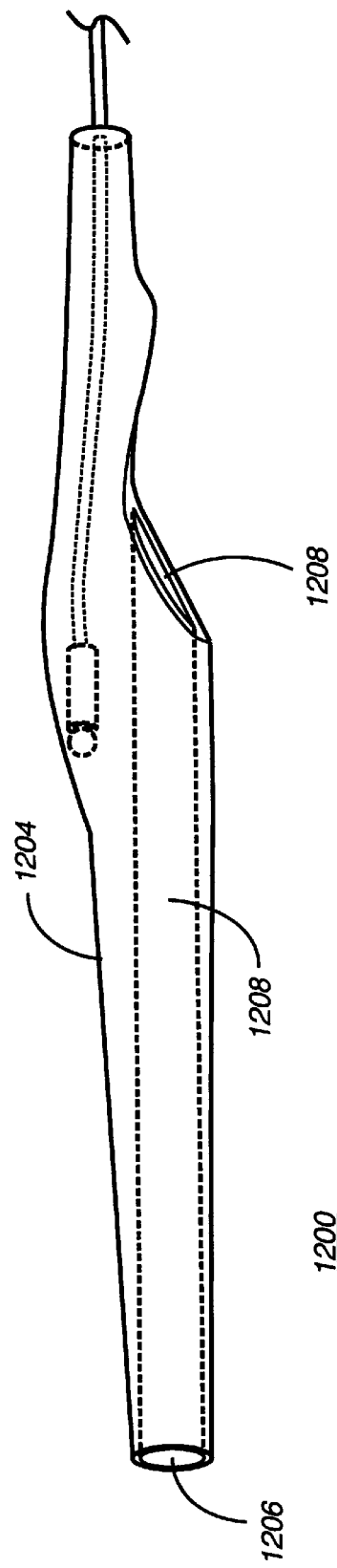
FIG. 12 highlights an alternate swivel housing assembly.

A better view of a skived proximal opening 1202 is shown in FIG. 12 which highlights an alternate swivel tip assembly

1200 having a slightly different housing shape. Housing 1204 includes a lumen 1208 having distal 1206 and proximal 1202 openings or ports.

Attached to the swivel housing 110 as shown in FIG. 1 is an attachment member 102 that is inserted into housing 110 via aperture 104. In the preferred embodiment attachment member 102 comprises a piece of wire. Wire 102 is made from 304 stainless steel, although other materials known in the art can be substituted therefor. Wire 102 attaches the housing 110 to a flexible elongate member such as a catheter (not shown). A section of wire 102 is preferably folded over as shown at its proximal end to allow for better attachment to a catheter (not shown). In the preferred embodiment, the swivel wire has an extension length 130 of approximately 5 mm (0.197inch). The proximal end of the wire 102 (folded over portion) can be attached to a catheter using an adhesive, heat bonding, or any one of a number of other conventional attachment techniques. Preferably the attachment of the wire 102 to the catheter is done at the distal end of the catheter, although in different designs the attachment point may vary.

Instead of using a stainless steel wire as the attachment member 102, other materials suitable for insertion into humans or animals and which would provide for a strong enough attachment so that the housing 110 does not break away from the catheter may be used. Stainless steel wire is the preferred material in this embodiment, given the way the swivel tip assembly is formed by heat flowing the plastic in a jacket or mold as will be discussed further below to form housing 110.

At the distal end of the swivel wire 102 is a substantially spherical member such as a ball or sphere 106. A bushing 108 which is attached to the housing prevents the wire 102 from detaching given that sphere 106 has a larger diameter than the diameter of the bushing's opening. Heating the end of swivel wire 102 in a fixture forms the ball tip 106. Any burrs that may form from this process are removed prior to insertion of the swivel wire 102 into housing 110.

Figure 4:
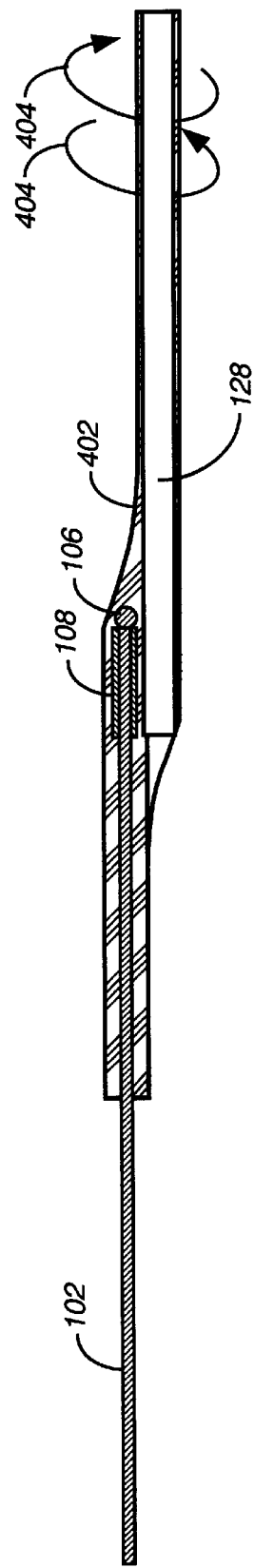
FIG. 4 shows a cross-sectional view of the swivel tip of FIG. 12.
Figure 5:
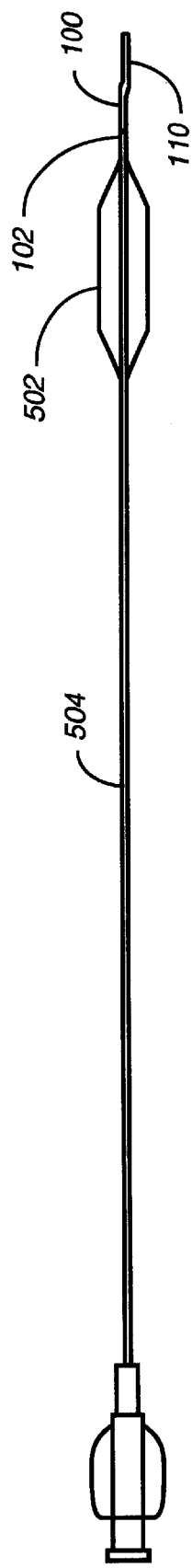
FIG. 5 shows a PCTA catheter having a swivel tip in accordance with the invention.

Alternatively, instead of making the ball 106 integral to swivel wire 102, ball tip 106 could be formed from a separate spherical member that is attached to swivel wire 102 by use of a number of known attachment techniques (e.g., welding, soldering, crimping, etc.). Alternatively to using a spherical member 106 as shown, any other shaped member (e.g., a cone shaped member, etc.) which would prevent the detachment of the attachment wire 102 from the rest of the swivel assembly 100, and would allow for the free rotation of the housing 110 about attachment member or wire 102 could be used. In close proximity to ball tip 106 is a bushing 108, which is slid into swivel wire 102 from the opposite end of swivel wire 102 until it reaches ball tip 106. Once the ball tip 106 and bushing 108 are inserted and pushed into to the end of aperture 104 which provides for a slip fit for ball tip 106 and bushing 108, the swivel tip housing 110 is heated using a hot torch fixture or other heat source. This heating causes the polyethylene housing to melt around the ball tip 106 and bushing 108 and fuses the bushing 108 and captures it within the housing 110. The preferred method of manufacturing the swivel tip assembly 100 will be discussed in detail further below. Once housing 110 is cooled, the swivel wire 102 is rotated (using the portion external to housing 110) causing ball tip 106 and swivel wire 102 to break free of any melted polyethylene which may have adhered to them. and to freely rotate about bushing 108. Bushing 108 which is firmly attached to housing 110 by the heating process prevents the detachment of swivel wire 102 from housing 110. Ball 106 and bushing 108 form a swivel or rotation point, which allows for housing 110 to swivel about wire 102. Although a ball and bushing have been utilized in the preferred embodiment, other designs which allow housing 110 to swivel or rotate about attachment joint designs may be used (e.g., a bearing encased in a housing member, etc.). In FIG. 2, the swivel wire 102 having ball tip 106 is shown. Swivel wire 102 in the preferred embodiment has a diameter 204 of approximately 0.15 mm +/−0.05 mm(0.006inch +/−0.0002 inch). The ball tip 106 has a diameter 206 of approximately 0.28 mm +/−0.025 mm (0.011-inch +/−0.001 inch). The overall length 202 of the swivel wire 102 and ball tip 106 is 38.1 mm +/−12.7 mm (1.5 inch +/−0.5 inch). In FIG. 3, bushing 108 is shown. Bushing 108 has a length 302 of approximately 1.52 mm (0.060 inch), an outside aperture diameter 304 of 0.33 mm +/−(0.013 +/−0.00135 inch) and an inside aperture diameter of 0.178 mm +/−0.0127 mm (0.007 +/−0.0005-inch). FIG. 4 shows a length wise cross-sectional view of the swivel tip assembly 1200 shown in FIG. 12. Swivel guide wire lumen housing 402 is different in shape than housing 110 shown in FIG. 1. Arrows 404 highlight the ability of housing 402 to rotate freely in either direction. In FIG. 5, there is shown a flexible elongate member assembly such as a swivel tipped PCTA catheter assembly 500 in accordance with the invention. Swivel tipped PCTA catheter 500 includes a PCTA catheter 504 as is known in the art (e.g., a VINTAGE™ PCTA catheter manufactured by Endosonics Corp.) and includes a swivel tip assembly 100 attached to the distal end of the PCTA catheter 504.

The proximal end of the swivel wire 102 is attached to the distal end of the PCTA catheter 504 by bonding the wire using adhesive. Other known attachment techniques such as welding or crimping the swivel wire 102 to the distal portion of catheter 504 can also be used depending on the particular design. In the embodiment shown, swivel tip assembly 100 is located distally of balloon 502.

The catheter with swivel tip assembly 500 in accordance with the present invention helps prevent the grabbing of the guide wire 116 as the catheter assembly 500 is tracked over the guide wire 116. The swivel or rotation action provided by the swivel tip assembly 100 helps reduce snagging of the guide wire 116 especially while the catheter assembly 500 is being tracked over a tight bend in a vessel (e.g., artery).

Figure 13:
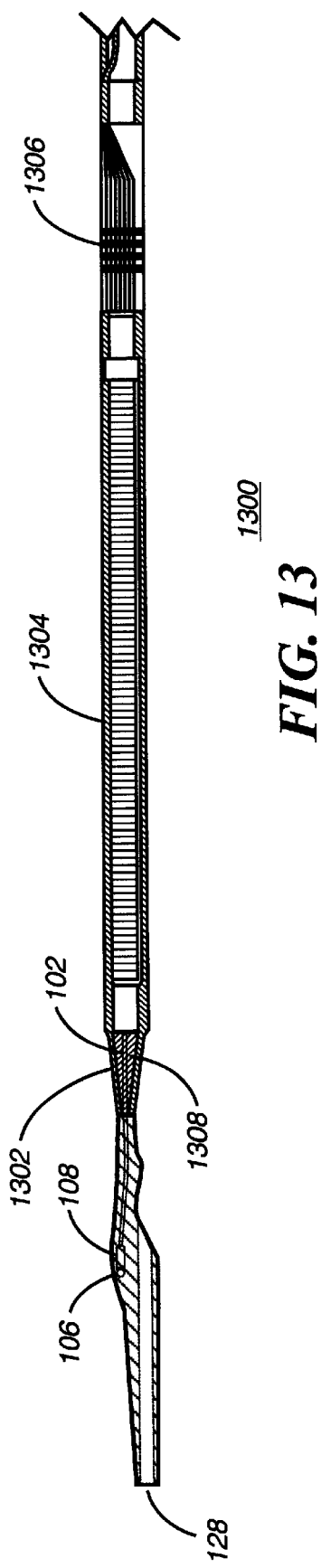
FIG. 13 shows a cross-sectional view of a portion of a radiation catheter using the swivel tip assembly of the present invention.

Referring now to FIG. 13, there is shown an radiation delivery catheter 1300 that includes a swivel tip assembly in accordance with the present invention. Similar to the catheter shown in FIG. 5, the proximal end of wire 102 is adhesively or heat bonded at location 1302 to the distal end of the catheter 1308. The guide wire lumen 128 allows the catheter 1300 to receive a guide wire (not shown). Radiation catheter 1300 includes a radiation section 1304, and an ultrasound section 1306 which provides internal images of the vessel to help guide the radiation treatment.

Figure 14:
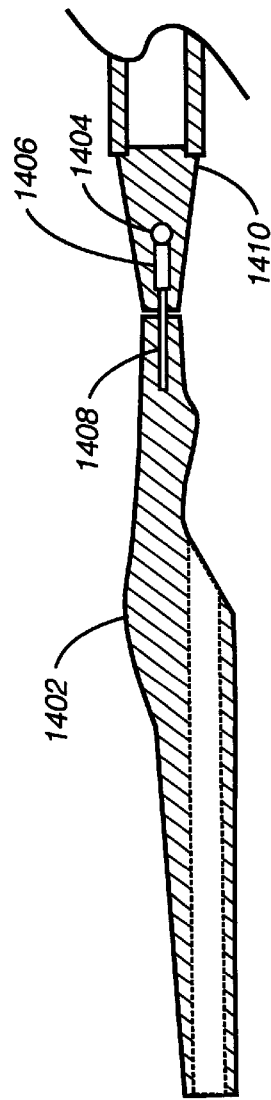
FIG. 14 shows a partial cross-sectional view of an alternate embodiment of a catheter having a swivel housing and the swivel joint is located within the catheter.

Although the above embodiments have shown the swivel joint, for example in FIG.1 comprising bushing 108 and sphere 106 located within the swivel housing, the swivel joint could be placed in the catheter in an alternate embodiment. This would cause the housing and attachment means to rotate or swivel about the guide wire. Such an embodiment is shown in FIG. 14. The swivel housing 1402 is attached to catheter 1410 via wire 1408 and a bushing 1406 and sphere 1404 are located within the catheter 1410. In still another embodiment, the swivel joint could be located between the swivel housing and distal end of the catheter and external to both.

Figure 6:
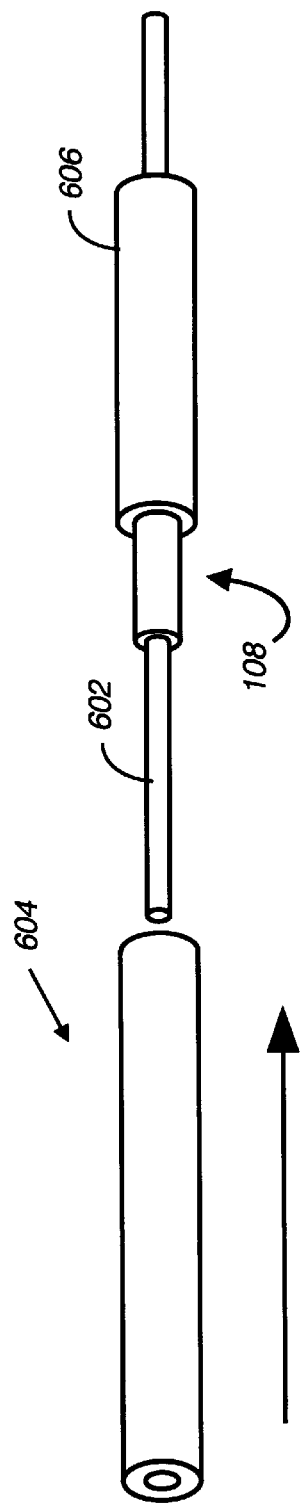
FIGS. 6–11 show some of the different manufacturing steps taken in order to manufacture the swivel tip assembly in accordance with the preferred embodiment of the invention.
Figure 7:
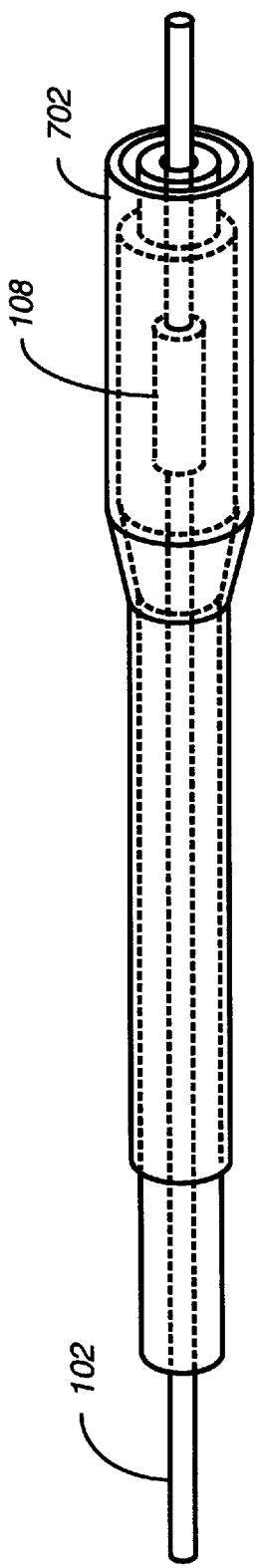

An overview of the preferred method of manufacture of the swivel tip assembly will now be discussed in order to further help the understand of the present invention. The manufacturing process starts by cutting to length, two pieces 604 and 606 of HDPE 0.009"×0.024" tubing to a length of approximately 5 cm each. The swivel bushing 108 is then slid over a 0.178 mm (0.007" mandrel) 602 then the two HDPE tubes 604 and 606 are inserted into the mandrel as shown in FIG. 6 on either side of the bushing 108. Next a Teflon™ forming jacket 702 is placed over the HDPE with the bushing 108 placed near the inner taper of the forming jacket 702 as shown in FIG. 7. The HDPE is then flowed inside of the forming jacket 702 using a heat torch operating at about 450° F., allowing for the HDPE to flow completely around the bushing 108. After the HDPE has cooled, the HDPE is trimmed flush to the larger side of forming jacket 702 using a blade.

Figure 8:
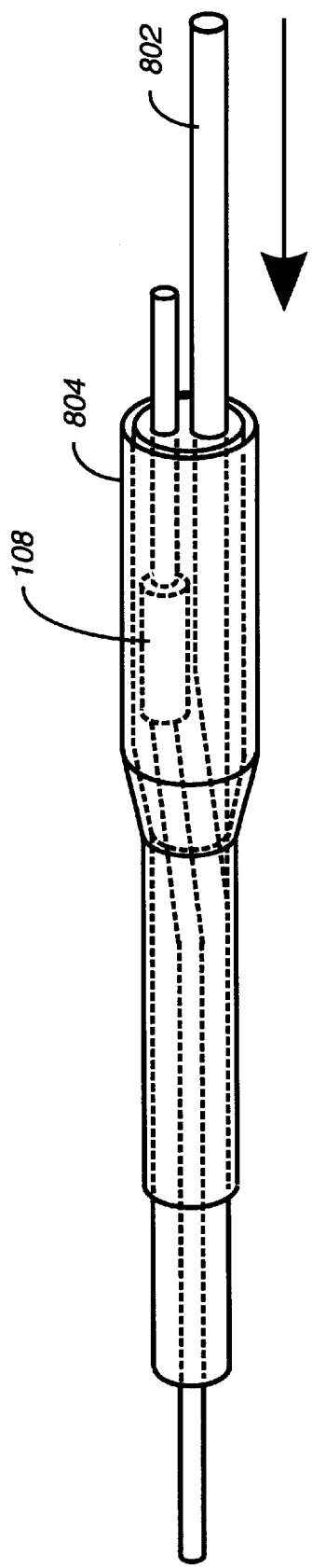
Figure 9:
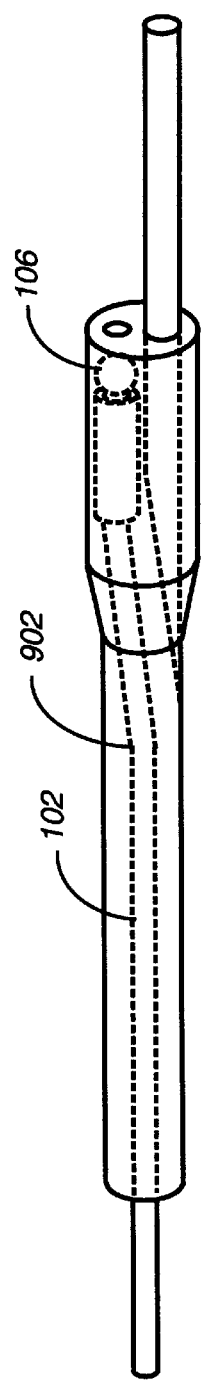
Figure 10:
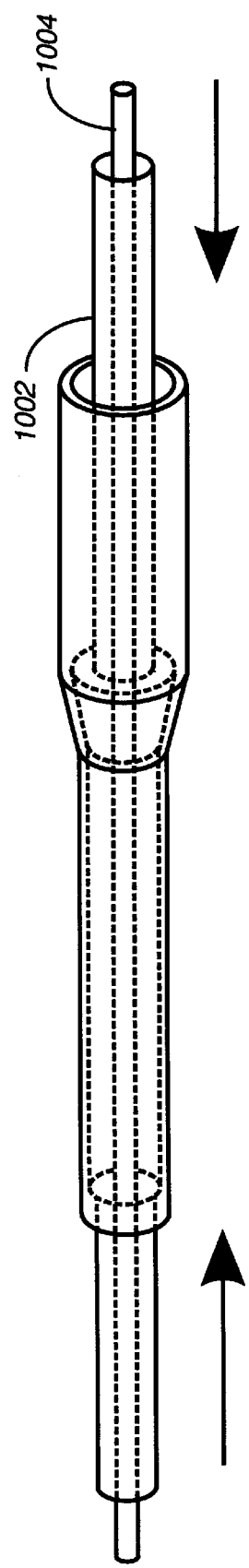

The swivel bushing side (distal) of the jacket is again heated to reflow the plastic, while the HDPE is still under the torch and flowing, a spearcut mandrel 802, as shown in FIG. 8, is inserted into the HDPE from the larger diameter side, spear side first. The spear is inserted with the spear face surface facing the bushing 108. Once the HDPE has cooled, the Teflon™ forming jacket 702 is removed. A ball tipped wire 902 comprising ball 106 and wire 102 is inserted into the distal side until the ball touches the bushing 108 as shown in FIG. 9. A piece of inner lumen 0.432 mm ×0.533 mm (0.017"×0.021") 1002 is cut to a length of approximately 8 cm. A 0.432 mm (0.017") mandrel 1004 is then inserted into the inner lumen 1002. A forming jacket is then slid over the center of the lumen as shown in FIG. 10. The jacket is then heated while both sides of the inner lumen are pushed inward until it fills the proximal end of the jacket and about 3 mm of the distal end. The jacket is then removed and the HDPE is removed off of the mandrel.

Figure 11:
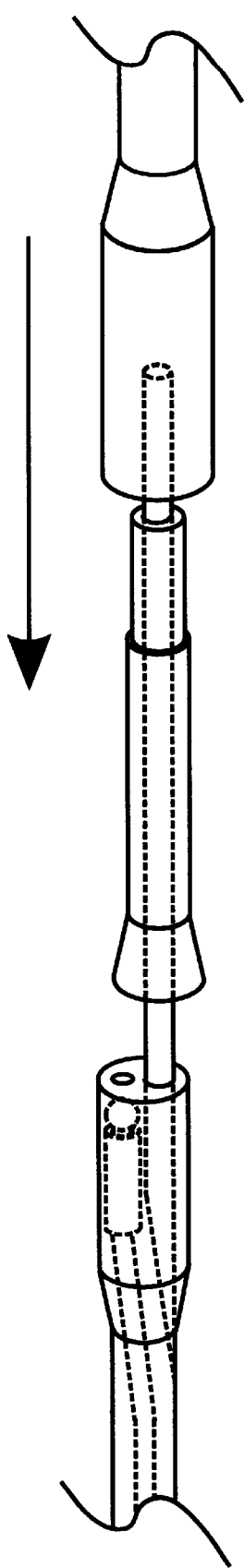

Next as shown in FIG. 11, the HDPE tube is slid over the spearcut mandrel until the flared end butts against the swivel bushing assembly. A forming jacket is slid over the distal HDPE and over the proximal swivel assembly until it stops. A heat torch is then used to heat the cone of the jacket only until the distal plastic fuses with the proximal plastic. The forming jacket is then removed and the proximal end of the swivel tip is trimmed where the ball tipped wire straightens out in the plastic. The spearcut mandrel is removed and the distal end of the swivel tip is trimmed so that its length is approximately 15 mm. The ball tipped wire protruding from the proximal side is then folded over so that the length of the protruding wire is approximately 5 mm. Finally, a skive is added to the housing as shown in FIG. 1.

While the invention has been described in conjunction with specific embodiments, it is evident that many alternatives, modifications, permutations and variations will become apparent to those skilled in the art in light of the foregoing description. For example, although the swivel tip assembly 100 has been shown using a sphere and bushing as the swivel point or joint for the swivel tip housing 110 other alternative swivel joints known in the art can be used. For example, a snap-in ball joint design could be used instead of using a bushing 108. Also, the swivel tip concept of the present invention can be utilized not only with a PCTA or radiation catheters as described above, it can be used with other types of flexible elongated members which can be inserted in patients or animals and that are tracked along a guide wire.

What is claimed is:

1. A catheter assembly comprising:

a catheter having a lumen;

a housing having a passageway for receiving a guide wire and for allowing the catheter assembly to track along the guide wire;

a swivel joint located within the housing; and the housing is attached to the catheter by a wire having one end attached to the swivel joint and the other end attached to the catheter.

2. A catheter assembly as defined in claim 1, wherein the housing is located distally of the catheter.

3. A catheter assembly as defined in claim 1, wherein the swivel joint allows the housing to rotate freely about the wire.

4. A catheter assembly as defined in claim 3, wherein the catheter has proximal and distal ends and the wire is attached to the catheter at the catheter's distal end.

5. A catheter assembly as defined in claim 3, wherein the swivel joint includes a bushing.

6. A catheter assembly as defined in claim 5, wherein the bushing is attached to the housing by melting the housing about the bushing.

7. A catheter assembly as defined in claim 5, wherein the wire further comprises a substantially spherical member at one end which is captured by the bushing.

8. A catheter assembly as defined in claim 1, wherein the wire and the housing's passageway are substantially parallel to each other.

9. A catheter assembly as defined in claim 1, wherein the housing is made from plastic.

10. A catheter assembly comprising:

a catheter having a lumen; and a housing having a passageway for receiving a guide wire and for allowing the catheter assembly to track along the guide wire, wherein the housing is attached to the catheter by a wire which is attached to a swivel joint located within the catheter that allows the housing to rotate about the wire.

11. A catheter assembly as defined in claim 10, wherein the housing is located distally of the catheter.

12. A catheter assembly as defined in claim 10, wherein the passageway has distal and proximal openings and the proximal opening is skived to help reduce the possibility of the guide hanging up with the housing.

13. A catheter assembly as defined in claim 10, wherein the wire and the housing's passageway are substantially parallel to each other.

14. A catheter assembly as defined in claim 10, wherein the housing is made from plastic.

15. A catheter assembly as defined in claim 10, wherein the swivel joint includes a bushing, which is fixed to the housing.

16. A catheter assembly as defined in claim 15, wherein the wire further comprises a substantially spherical member at one end which is captured by the bushing.

* * * * *